United States Patent [19]
Yundt

[11] Patent Number: 5,734,591
[45] Date of Patent: *Mar. 31, 1998

[54] METHOD OF ANALYZING MULTIPLE RANGE TEST DATA

[75] Inventor: John C. Yundt, Plano, Tex.

[73] Assignee: Xyletech Systems, Inc., Plano, Tex.

[*] Notice: The term of this patent shall not extend beyond the expiration date of Pat. No. 5,541,854.

[21] Appl. No.: 688,493

[22] Filed: Jul. 30, 1996

Related U.S. Application Data

[63] Continuation-in-part of Ser. No. 67,023, May 26, 1993, Pat. No. 5,541,854.

[51] Int. Cl.$^6$ ...................................................... G06K 11/00
[52] U.S. Cl. ................ 364/551.01; 395/140; 346/33 ME
[58] Field of Search .......................... 364/551.01, 413.07, 364/413.08; 395/140, 141; 340/825.06; 346/33 ME, 66

[56] References Cited

U.S. PATENT DOCUMENTS 5,541,854  7/1996  Yundt .................................. 364/551.01

*Primary Examiner*—Emanuel T. Voeltz
*Assistant Examiner*—Thomas Peeso
*Attorney, Agent, or Firm*—Shook, Hardy & Bacon L.L.P.

[57] ABSTRACT

A method is disclosed for analyzing the performance of a testing device for analyzing biochemical samples or human bodily fluids which operates over at least two ranges. The method of the present invention comprises obtaining a first set of test results relating to the biochemical samples from the testing device over at least two ranges, and calculating from the first set of test results an individual range mean for each of the at least two ranges. The method also includes obtaining a second set of test results relating to the biochemical samples from a group of testing devices that operate over the at least two ranges, calculating from the second set of test results a group range mean and a group range standard deviation for each of the at least two ranges, and calculating standard deviation indexes for the testing device from the individual range means, the group range means and the group range standard deviations. The method further comprises forming generally parallel spaced apart data range axes, each relating to a range of operation of the testing device, to facilitate analysis of the performance of the testing device over each range of operation, wherein the respective positions of the data range axes in relation to one another are scaled based on the values of the operating ranges, and then plotting all of the standard deviation indexes in relation to the data range axes in such a way that analysis of the performance of the testing device over the at least two operating ranges is provided in a single graphic display.

40 Claims, 12 Drawing Sheets

| | INDIVIDUAL DEVICE | | | | GROUP | | |
|---|---|---|---|---|---|---|---|
| | MEAN | S.D. | C.V. | S.D.I. | MEAN | S.D. | C.V. |
| I | 20.92 | 1.13 | 5.39 | -0.52 | 21.6 | 1.31 | 6.06 |
| II | 51.92 | 2.00 | 3.85 | -0.41 | 52.9 | 2.39 | 4.52 |
| III | 83.6 | 1.84 | 2.20 | -0.64 | 85.2 | 2.50 | 2.94 |

METHOD OF ANALYZING MULTIPLE RANGE TEST DATA

CROSS-REFERENCE TO RELATED APPLICATION

This application is a continuation-in-part of U.S. patent application Ser. No. 08/067,023, filed May 26, 1993, now U.S. Pat. No. 5,541,854.

FIELD OF THE INVENTION

This invention relates to a method of analyzing test data, and more particularly, to a method of analyzing test data of equipment having a multilevel control system to thereby determine if the equipment is operating properly.

BACKGROUND OF THE INVENTION

Hematology equipment is used to analyze the blood of a patient. As with most equipment, it is necessary to calibrate the hematology equipment to obtain accurate test results. The need to calibrate hematology equipment has become increasingly important due to recent legislative enactments which have required more frequent monitoring of the equipment to ensure proper calibration. The heightened legislative attention to accurate hematology equipment performance is due, no doubt, to the substantial escalation of severe transmittable blood diseases, and in particular, the AIDS virus. The more stringent calibration requirements are therefore certainly prudent, but nevertheless have significantly increased the calibration burden for users of laboratory equipment.

FIG. 1 shows three prior art graphs used for analyzing the operation of a hematology testing device. The graphs of FIG. 1 are commonly referred to as Levey-Jennings plots. As noted at the top of each graph in FIG. 1, each graph depicts data from a particular "assayed range." Depending on the age of the patient, the test results produced by a particular hematology testing device vary significantly in value. A hematology testing device must therefore produce accurate tests results over multiple ranges, and thus, must be calibrated to ensure proper operation over each range.

Referring to FIG. 1(a), the graph depicts the test results of a particular hematology testing device over the "assayed range" of 18 to 24. The various test points, such as point 10, represent particular test results from patient blood analyses taken by a particular hematology device. FIG. 2 shows a table summarizing the results of the data from the graphs of FIG. 1. The mean for the data given in FIG. 1(a) is 20.92 and the standard deviation is 1.13. The table of FIG. 2 also includes data relating to results from a group of hematology devices so that the results of the particular hematology device can be compared to the performance of the group of hematology devices as a whole. The average performance of a group of hematology devices is believed to be an effective method for evaluating the performance of a particular hematology device. If the particular device deviates significantly from the average performance characteristics of the group, this result indicates a problem with the performance of the particular device. Likewise, if the performance of the particular device substantially corresponds with the average performance of the group, this result indicates that the particular device is operating property and does not require calibration.

The graphs of FIG. 1 have three regions 12, 14, and 16, graphically depicted by shading, and being centered around the line 17 corresponding to the mean for the data of the group of hematology testing devices over the particular level or assayed range. The dark shading indicates data in an unacceptable range; the region without shading indicates data in an acceptable range; and the slightly shaded region indicates data that is borderline, and therefore may or may not be acceptable. The shading is particularly helpful because it provides a readily identifiable visual indicator of the significance of each data point. In short, the graphs of FIG. 1 and the table of FIG. 2 facilitate calibration of a particular hematology testing device. Nevertheless, analyzing the performance of a hematology device required analysis of multiple graphs (i.e., one graph for each data range).

In an effort to allow multiple hematology devices to be analyzed at the same time, another prior art graph was developed (shown in FIG. 3) and is commonly referred to as a Youden Plot. The Youden Plot allows multiple hematology testing devices to be analyzed over two assayed ranges, and was thus a meaningful advance in the art of calibrating hematology testing devices. Referring to FIG. 3, the vertical axis of the graph is centered about the man of the group data for the assayed range of 18 to 24 (i.e., 21.6), and the horizontal axis is centered about the mean of the group data for the assayed range of 46 to 58 (i.e., 52.9). Point 20 corresponds to the data point for the hematology testing device data from the graphs of FIGS. 1(a)&(b) and the table of FIG. 2. The horizontal darkened line 22 corresponds to the mean of the data (i.e., 20.92) of the hematology device over the range of 18 to 24, and the vertical darkened line 24 corresponds to the mean of the data (i.e., 51.92) of the hematology device over the range of 46 to 58. As shown, the data point 20 is in the unshaded region for both the horizontal and vertical axes, and thus demonstrates that the mean for the hematology device over both ranges is acceptable. The remaining data points, such as points 30, 32, and 34, correspond to the mean values of other hematology devices over the ranges of 18 to 24 and 46 to 58.

A significant limitation of the Youden Plot is that only two ranges of data can be analyzed. As explained above, hematology devices operate over multiple ranges to accommodate varying data ranges of blood test results due to such variables as the varying ages of patients. Thus, to completely analyze and calibrate a particular hematology device, several graphs typically must be analyzed. A further limitation of the Youden Plot is that the horizontal and vertical axes are obviously perpendicular, and thus it is very difficult to analyze the linear performance of the hematology device over both ranges depicted on the plot. Each of these limitations are, likewise, common to the Levey-Jennings plots.

While the limitations above have been described in the context of a hematology device, the limitations apply to all devices having multilevel control systems, or stated another way, devices which operate over multiple ranges. The majority of body fluid chemistry analysis devices implement multilevel control systems, and thus suffer from the above-described limitations.

SUMMARY OF THE INVENTION

It is therefore an object of the present invention to provide a method for improving and facilitating the analysis of the performance of equipment or devices which have multilevel control systems. Another object is to provide a method which allows for efficient and effective analysis of such equipment over all operational ranges of the equipment to alleviate the need to analyze multiple graphs to calibrate the equipment.

And yet another object is to provide a method for graphing the test results of such equipment which facilitates analysis of the linear operation of the equipment over all ranges of operation of the equipment. A related object is to provide a method of graphing the test results of the equipment performance to allow persons to efficiently and accurately analyze the results to determine if the equipment is operating properly without the need for sophisticated training.

A further object is to disclose a graph and a method of using such a graph which facilitates analysis of devices operating over multiple ranges, and which method of graphing and analyzing is also more efficient and less time consuming than prior art analytical methods.

To accomplish these and related objects, a method is disclosed for analyzing the performance of a testing device for analyzing biochemical samples or human bodily fluids which operates over at least two ranges. The method of the present invention comprises obtaining a first set of test results relating to the biochemical samples from the testing device over at least two ranges, and calculating from the first set of test results an individual range mean for each of the at least two ranges. The method also includes obtaining a second set of test results relating to the biochemical samples from a group of testing devices that operate over the at least two ranges, calculating from the second set of test results a group range mean and a group range standard deviation for each of the at least two ranges, and calculating standard deviation indexes for the testing device from the individual range means, the group range means and the group range standard deviations. The method further comprises forming generally parallel spaced apart data range axes, each relating to a range of operation of the testing device, to facilitate analysis of the performance of the testing device over each range of operation, wherein the respective positions of the data range axes in relation to one another are scaled based on the values of the operating ranges, and then plotting all of the standard deviation indexes in relation to the data range axes in such a way that analysis of the performance of the testing device over the at least two operating ranges is provided in a single graphic display.

The analysis method described for hematology devices applies equally as well to any device having a multilevel control system. The above-described method overcomes the problems of the prior art by allowing analysis of all operational ranges of devices having multilevel control systems. The method also significantly facilitates analysis of the linear performance of such devices over all operational ranges. Moreover, the method is more efficient than the prior art analysis methods because only one graph is required to perform calibration analysis over all operational ranges, in contrast to the multiple graphs required by prior art methods to calibrate multilevel control system devices.

BRIEF DESCRIPTION OF THE DRAWINGS

In the accompanying drawings which form a part of the specification and are to be read in conjunction therewith, and in which like reference numerals are used to indicate like parts in the various views:

FIG. 3 is a prior art Youden plot displaying data for two ranges of performance of the device;

DETAILED DESCRIPTION OF THE PREFERRED EMBODIMENTS

Figure 1A:
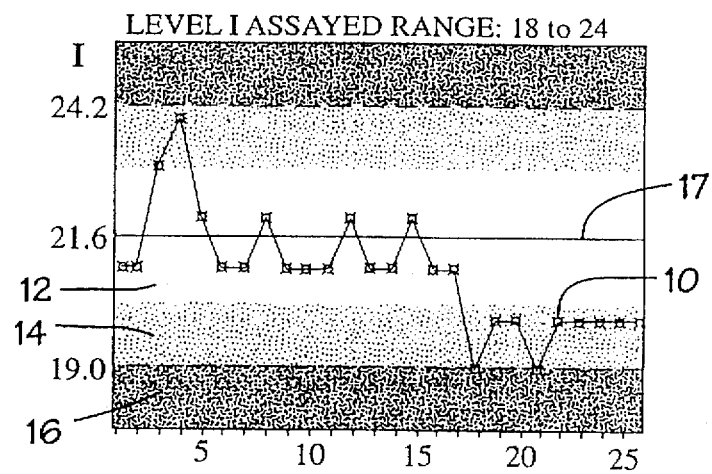
FIGS. 1a–1c show three prior art graphs for data of a device having a multilevel control system, and each graph displays data corresponding to a particular range of operation of the device.
Figure 1B:
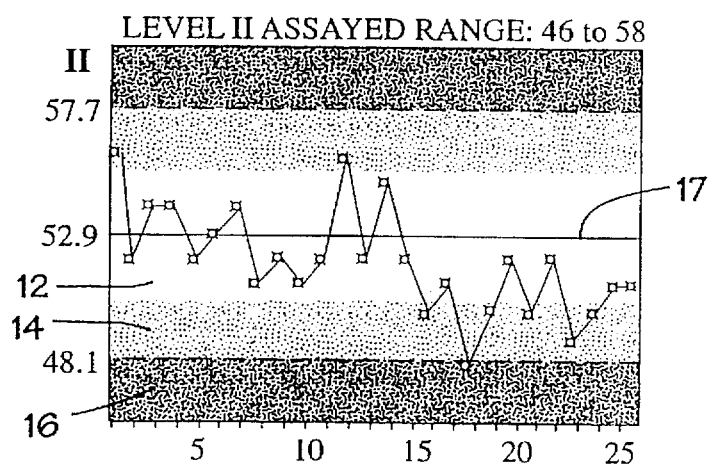
Figure 1C:
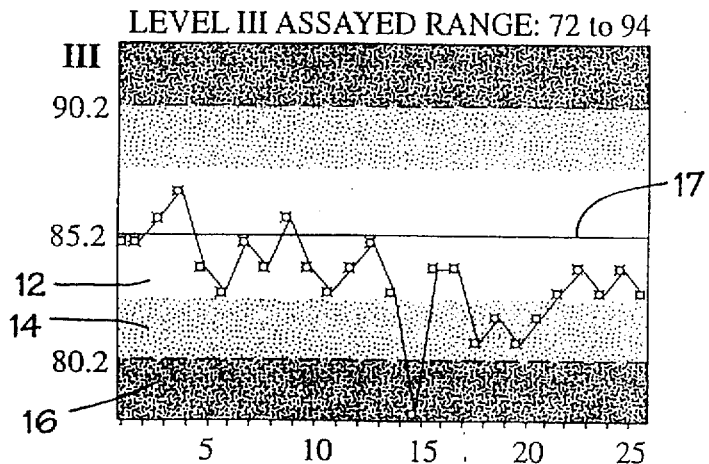
Figure 2:
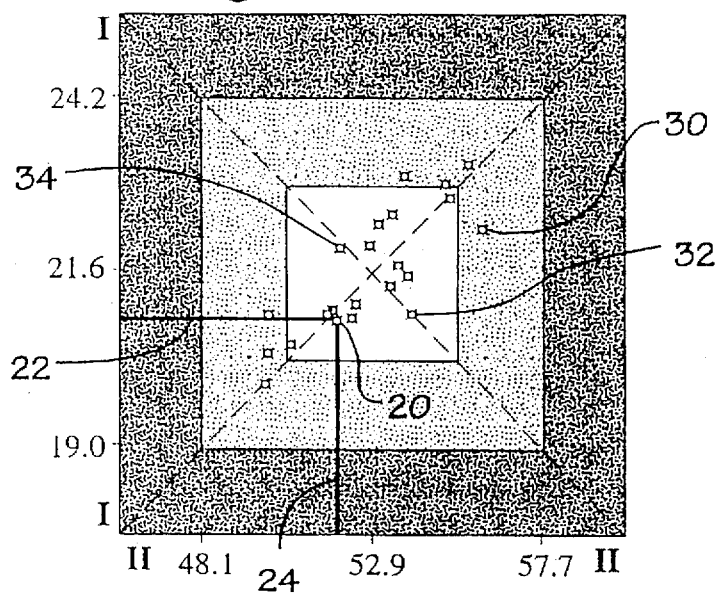
FIG. 2 is a table of the data plotted for each of the graphs in FIG. 1.
Figure 4:
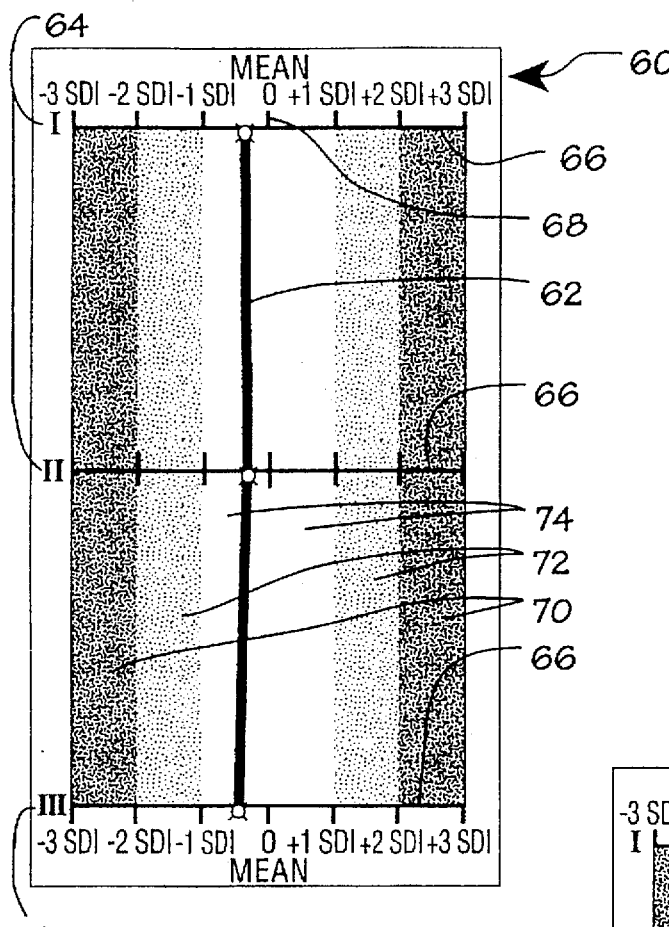
FIG. 4 shows a preferred embodiment of the graph of the present invention used in the method for analyzing the performance of a multilevel control system device.

Referring now to FIG. 4, the graph required for implementing the method of the present invention is designated generally 60. The darkened line 62 is a plot of the SDI data contained in the table of FIG. 2. As described above, the data of that table relates to the operation of a device which operates over at least two assayed ranges, and for purposes of illustration, those ranges comprise: 18 to 24, 46 to 58, and 72 to 94. Referring to FIG. 2, Roman numerals are used to designate corresponding data ranges and are designated by Arabic numeral 64.

The graph 60 of FIG. 4 is created by forming generally parallel spaced apart data range axes 66 for each range of data. Graph 60 comprises three data range axes 66, one axis corresponding to each of the data ranges of the table in FIG. 2. Roman numerals 64 corresponding to each data range axis 66 correlate to the Roman numerals associated with each data range in the table of FIG. 2. The method of creating the graph 60 further comprises forming an axis 68 in generally orthogonal relation to the data range axes 66.

In the preferred embodiment, the data range axes are labeled with standard deviation index (SDI) units. To calculate the SDI for each range of data for a device which operates over at least two ranges, such as a hematology device, the following data must be gathered: (1) mean of the data for each range for each hematology device; (2) mean for each range for the group of hematology devices; and (3) standard deviation for each range for the group of hematology devices. The SDI for each range for each hematology device is calculated according to the following equation:

$$\frac{\text{(particular hematology device range mean} - \text{group range mean)}}{\text{(group range standard deviation)}}$$

For instance, referring to the table of FIG. 2, the implementation of the equation to calculate the SDI for range I is as follows:

$$\frac{(20.92 - 21.6)}{(1.31)} = -0.52$$

As is well known in the art, the mean is a measure of the overall tendency of the data group, also known as the average. The standard deviation is a measure of the average distance that particular data points in the group deviate from the mean. The SDI, as is apparent from the equation, measures how far away the particular device mean is from the group mean in terms of the group standard deviation. Unitizing the difference between the group mean and the particular device mean by group standard deviation allows for comparison of the data for a particular device to the data of the group. An SDI of +1 results from a testing system mean being one group standard deviation above the group mean. An SDI of 0 results from a testing system mean matching the group mean, and an SDI of −1 results from a testing system mean being one group standard deviation below the group mean. A testing system mean which is two standard deviations away from the group mean (i.e., either an SDI of +2 or −2) is typically considered abnormal, thus evidencing a problem with the operation of the device. An SDI of +1 or −1 presents a borderline reading which may be problematic, but not critically so.

The regions between plus or minus 2 SDIs and plus or minus 3 SDIs, respectively, are designated 70 in FIG. 4. Visible indicia is provided within the regions 70, preferably, in the form of a dark shading. The regions between the plus or minus 1 SDI and the plus or minus 2 SDI, respectively, are designated 72. Region 72 is marked with a unique visible indicia, which in the preferred embodiment is a shading lighter than that of regions 70. The regions between 0 SDI and plus or minus 1 SDI are designated 74. The regions 74 are provided with a unique visible indicia, which preferably comprises a shading lighter than that of regions 70 and 72, and more specifically, preferably comprises no shading, as shown in FIG. 4.

Figure 5:
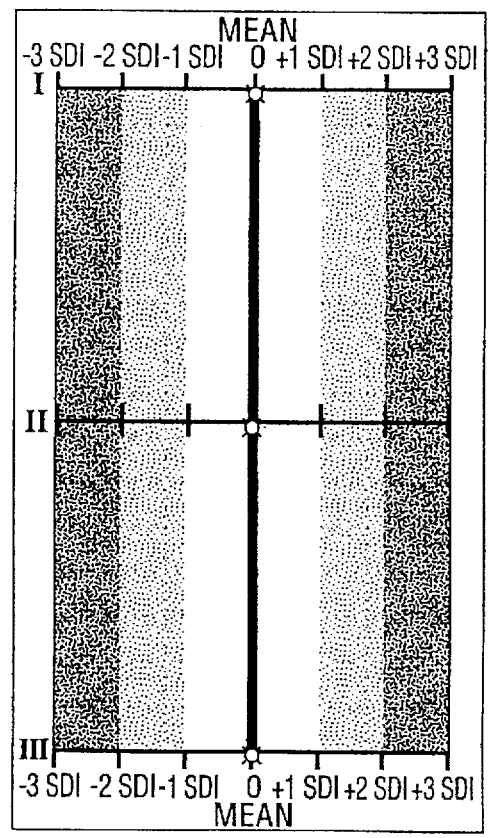
FIG. 5 shows the method step of plotting data from a multilevel control system device on the graph of FIG. 4.
Figure 6:
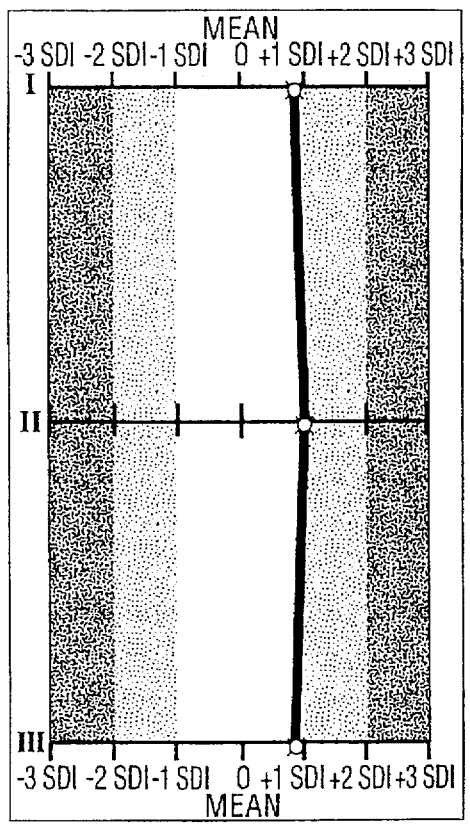
FIG. 6 shows the method step of plotting data from a multilevel control system device on the graph of FIG. 4.
Figure 7:
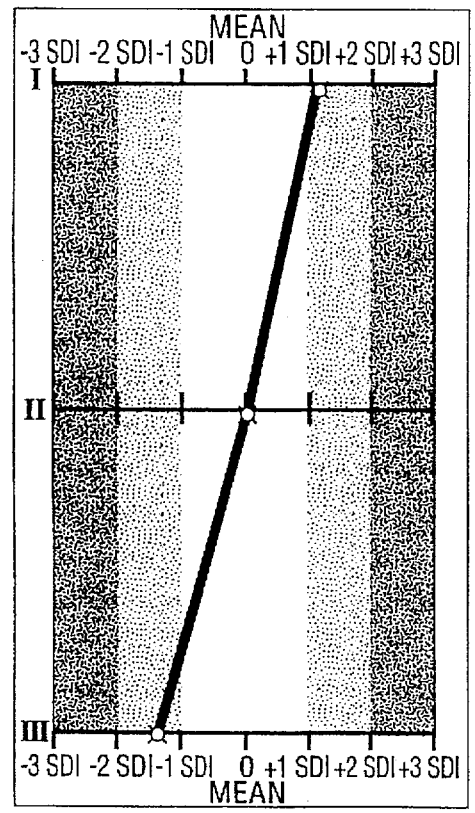
FIG. 7 shows the method step of plotting data from a multilevel control system device on the graph of FIG. 4.
Figure 8:
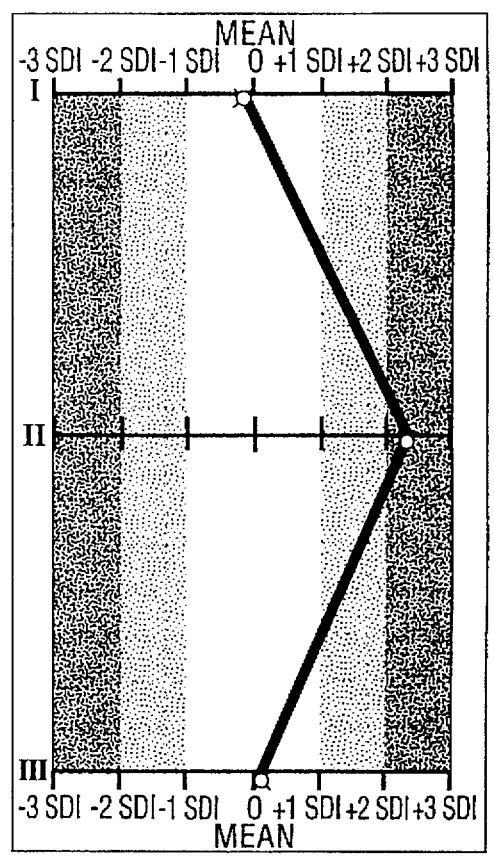
FIG. 8 shows the method step of plotting data from a multilevel control system device on the graph of FIG. 4.

FIGS. 5–7 are particular plots of data on the graph 60. The plot in FIG. 5 demonstrates a plot of a device which matched the group device mean for each data range. The plot in FIG. 6 demonstrates the plot of a device which is recovering control values consistently higher than the group mean. All three data ranges are running almost one group SDI above the group mean. This indicates a significant positive bias in the testing device which should be evaluated for cause. The plot in FIG. 7 demonstrates a plot for a device which is recovering higher control values than the group at range I, the same control values as the group at range II, and lower control levels than the group at range III. This plot indicates a linearity problem with the testing system because the testing device behaves differently at different operational ranges. The plot of FIG. 8 demonstrates the plot of a testing device with a different type of linearity problem. The device is close to the group mean at ranges I and III, but is recovering significantly higher control values than the group mean at range II.

In analyzing the graph 60, there are two important considerations: (1) the angle of the line, and the (2) region designated by shading in which the line lies. The angle of the line is a measure of the device's linear performance. A bent or sloping line indicates that the device is not behaving the same across different ranges of performance. As explained above, the dark shaded, light shaded, and nonshaded regions, designated 70, 72, and 74, respectively, correspond to problem action levels, possible problem action levels, and no problems, respectively.

A straight line down in the dark shaded region, such as regions 70, indicates a significant bias in the testing device. If the plot is angular with some of the points (or all) falling in the shaded regions, the degree of shading indicates the significance of the linearity distortion.

Figure 9:
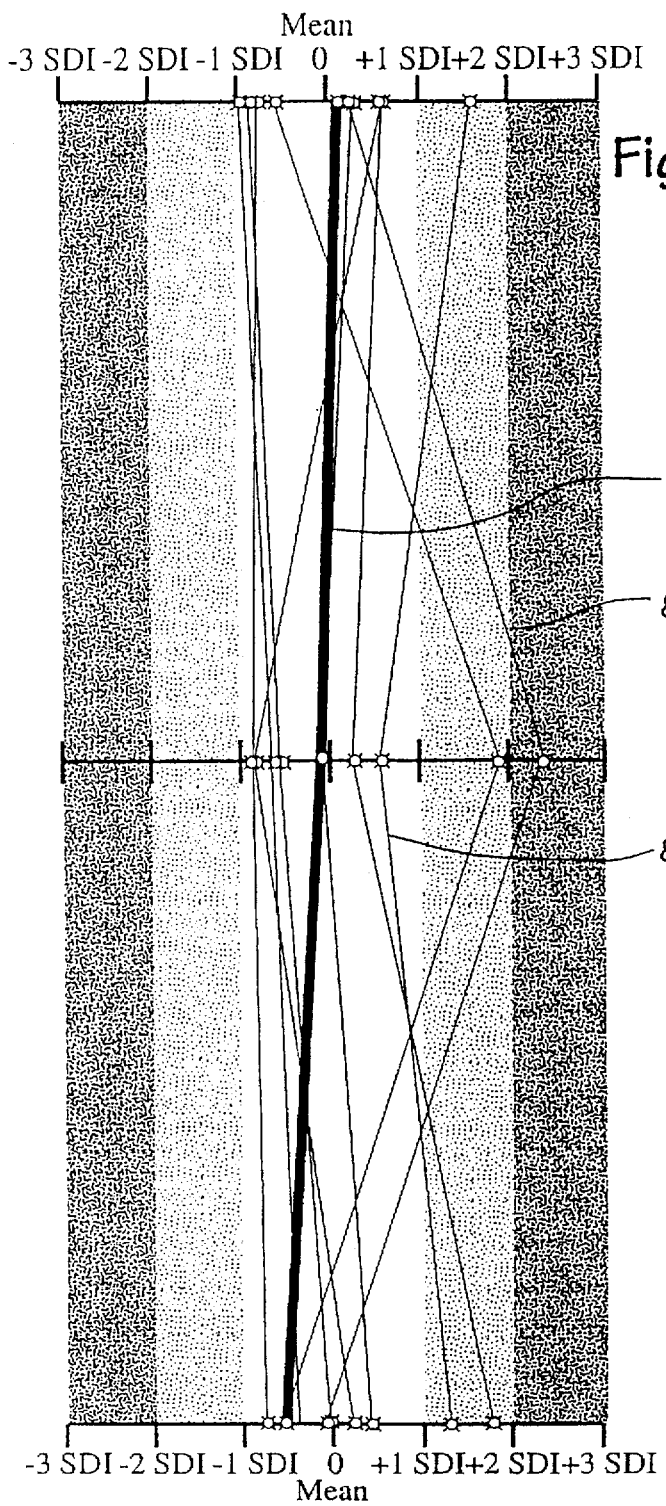
FIG. 9 shows the method step of plotting data from a group of multilevel control system devices on the graph of FIG. 4.

Referring to FIG. 9, an additional graph 60 is shown in which the performance of a particular device is designated by the thick line 83, and the performance of the other devices of the group are indicated by the thin lines, such as lines 84 and 86. The graph of FIG. 9 allows the performance of a particular hematology device to be readily compared to the performance of all hematology devices of the group.

To plot the data on the graph shown in FIG. 4, the following computer program can be implemented on a computer:

```
/* yundtplt.c */
/*
This program was coded for Borland C++ Version 3.1.
The compile/link command line was:
bcc yundtplt.c att.obj cga.obj egavga.obj herc.obj ibm8514.obj pc3270.obj
graphics.lib
*/
#include <stdio.h>
#include <stdlib.h>
#include <io.h>
#include <dos.h>
#include <ctype.h>
#include <graphics.h>
#include <conio.h>
#define TRUE 1
#define FALSE 0
/* #function proto-types */
void init_graphics(void);
void draw_yp_outline(void);
void show_err_msg(char *s);
void read_study_stats(double gmean[ ],double gsd[ ],double lmean[ ]);
void write_study_stats(double gmean[ ],double gsd[ ], double lmean[ ]);
void calc_sdis(double gmean[ ],double gsd[ ],double lmean[ ],double lsdi[ ]);
void draw_dot(void);
```

-continued

```
void plot_yp(double lsdi[ ]);
int quit(void);
int do_more(void);
void get_lab_mean(double *mean);
void get_new_lmeans(double gmean[ ],double lmean[ ]);
void print_help_screen(void);
int main(void);
/* end of proto-types */
/* this routine will initialyze the graphics system to the highest resolution
available using the auto-detect mode.
Drivers ATT, CGA, EGAVGA, Herc, IBM8514, PC3270 must be linked in for
this code to work.        */
void init_graphics(void){
    int driver; /* Driver Type */
    int mode; /* Mode Type */
    registerbgidriver(ATT_driver);
    registerbgidriver(CGA_driver);
    registerbgidriver(EGAVGA_driver);
    registerbgidriver(Herc_driver);
    registerbgidriver(IBM8514_driver);
    registerbgidriver(PC3270_driver);
    driver = DETECT;
    mode = 0;
    initgraph(&driver,&mode,"");
}
/* this routine will draw the basic yundt plot outline. The plot
is drawn relative to the number of pixels in the target.
    The width of the plot is 3/4 the horizotal number of pixels
    positioned 1/10 the number of horizontal pixels from the left side.
    The height of the plot is 3/4 the vertical number of pixels
    positioned 1/8 the number of vertical pixels from the top.
    The labels are done in the default 8 × 8 pixel font.
    If the file MONO.FLG exists in the current directory, only
    black and white will be used instead of colors.
*/
void draw_yp_outline(void){
    int max_x; /* Number of horizotal pixels */
    int max_y; /* Number of vertical pixels */
    max_x = getmaxx( );
    max_y = getmaxy( );
    cleardevice( );
    /* setup line/color charateristics */
    setlinestyle(SOLID_LINE,0,NORM_WIDTH);
    setcolor(WHITE);
    /* color sdi areas if MONO.FLG does not exist */
    if(access("MONO.FLG",0)!=0){
        setfillstyle(SOLID_FILL,RED);
        bar(max_x/10,max_y/8,2*max_x/10,7*max_y/8);
        bar(6*max_x/10,max_y/8,7*max_x/10,7*max_y/8);
        setfillstyle(SOLID_FILL,YELLOW);
        bar(2*max_x/10,max_y/8,3*max_x/10,7*max_y/8);
        bar(5*max_x/10,max_y/8,6*max_x/10,7*max_y/8);
        setfillstyle(SOLID_FILL,GREEN);
        bar(3*max_x/10,max_y/8,5*max_x/10,7*max_y/8);
    }
    else{
    /* otherwise use patterns */
        setfillstyle(HATCH_FILL,WHITE);
        bar(max_x/10,max_y/8,2*max_x/10,7*max_y/8);
        bar(6*max_x/10,max_y/8,7*max_x/10,7*max_y/8);
        setfillstyle(CLOSE_DOT_FILL,WHITE);
        bar(2*max_x/10,max_y/8,3*max_x/10,7*max_y/8);
        bar(5*max_x/10,max_y/8,6*max_x/10,7*max_y/8);
        setfillstyle(EMPTY_FILL,BLACK);
        bar(3*max_x/10,max_y/8,5*max_x/10,7*max_y/8);
    }
    /* apply labels for level 1 area and outline */
    moveto(max_x/10,max_y/8);
    linerel(0,-10);
    linerel(0,10);
    linerel(6*max_x/10,0);
    linerel(0,-10);
    outtextxy(max_x/10 - 25,max_y/8 - 20,"-3 SDI");
    moveto(2*max_x/10,max_y/8);
    linerel(0,-10);
    outtextxy(2*max_x/10 - 25,max_y/8 - 20,"-2 SDI");
    moveto(3*max_x/10,max_y/8);
    linerel(0,-10);
    outtextxy(3*max_x/10 - 25,max_y/8 - 20,"-1 SDI");
    moveto(4*max_x/10,max_y/8);
```

```
        linerel(0,-10);
        /*
        linerel(0,6*max_y/8 + 20);
        */
        outtextxy(4*max_x/10 - 16,max_y/8 - 30,"Mean");
        outtextxy(4*max_x/10 - 4,max_y/8 - 20,"0");
        moveto(5*max_x/10,max_y/8);
        linerel(0,-10);
        outtextxy(5*max_x/10 - 25,max_y/8 - 20,"+1 SDI");
        moveto(6*max_x/10,max_y/8);
        linerel(0,- 10);
        outtextxy(6*max_x/10 - 25, max_y/8 - 20,"+2 SDI");
        outtextxy(7*max_x/10 - 25, max_y/8 - 20,"+3 SDI");
        outtextxy(7*max_x/10 + 5, max_y/8," Level I");
        /* apply labels for level 2 area and outline */
        moveto(max_x/10,4*max_y/8);
        linerel(0,-10);
        linerel(0,20);
        linerel(0,-10);
        linerel(6*max_x/10,0);
        linerel(0,-10);
        linerel(0,20);
        moveto(2*max_x/10,4*max_y/8);
        linerel(0,-10);
        linerel(0,20);
        moveto(3*max_x/10,4*max_y/8);
        linerel(0,-10);
        linerel(0,20);
        moveto(4*max_x/10,4*max_y/8);
        linerel(0,-10);
        linerel(0,20);
        moveto(5*max_x/10,4*max_y/8);
        linerel(0,-10);
        linerel(0,20);
        moveto(6*max_x/10,4*max_y/8);
        linerel(0,-10);
        linerel(0,20);
        outtextxy(7*max_x/10 + 5,4*max_y/8," Level II");
        /* apply labels for level 3 area and outline */
        moveto(max_x/10,7*max_y/8);
        linerel(0,+10);
        linerel(0,-10);
        linerel(6*max_x/10,0);
        linerel(0,+10);
        outtextxy(max_x/10 - 25,7*max_y/8 + 14,"-3 SDI");
        moveto(2*max_x/10,7*max_y/8);
        linerel(0,+10);
        outtextxy(2*max_x/10 - 25,7*max_y/8 + 14,"-2 SDI");
        moveto(3*max_x/10,7*max_y/8);
        linerel(0,+10);
        outtextxy(3*max_x/10 - 25,7*max_y/8 + 14,"-1 SDI");
        moveto(4*max_x/10,7*max_y/8);
        linerel(0,+10);
        outtextxy(4*max_x/10 - 16,7*max_y/8 + 26,"Mean");
        outtextxy(4*max_x/10 - 4,7*max_y/8 + 14,"0");
        moveto(5*max_x/10,7*max_y/8);
        linerel(0,+10);
        outtextxy(5*max_x/10 - 25,7*max_y/8 + 14,"+1 SDI");
        moveto(6*max_x/10,7*max_y/8);
        linerel(0,+10);
        outtextxy(6*max_x/10 - 25,7*max_y/8 + 14,"+2 SDI");
        outtextxy(7*max_x/10 - 25,7*max_y/8 + 14,"+3 SDI");
        outtextxy(7*max_x/10 + 5,7*max_y/8," Level III");
}
/* this routine will display the passed message s in textmode, beep,
and wait for the user to press a key */
void    show_err_msg(char *s){
    printf(s);
    sound(1000);
    sleep(2);
    nosound( );
    getch( );
}
/* this routine will read the peer group study data from a file named
pgstudy.dat. "pgstudy.dat" must exist and contain 9 doubles in it or
critical error will occur.
"pgstudy.dat" should contain data in the format:
level 1 group mean, level 1 group SD, level 1 lab mean
level 2 group mean, level 2 group SD, level 2 lab mean
level 3 group mean, level 3 group SD, level 3 lab mean.
```

```
The parameters gmean[ ],gsd[ ]and lmean[ ]must all be double arrays
of length 3 which will be loaded respectively with group mean data,
group SD data, and lab mean data for each level.
void    read_study_stats(double gmean[ ],double gsd[ ],double lmean[ ]){
        FILE *fp;       /* File Pointer for Data File */
        int level;      /* Level of Control */
        printf("Reading pgstudy.dat\n");
        fp = fopen("pgstudy.dat","r");
        if(fp == NULL){
        show_err_msg("Cannot open pgstudy.dat - ABORTING - press any key.");
        quit( );
        }
        for(level=0;level<3;level++){
        if(fscanf(fp,"%lf%lf%lf",&gmean[level],&gsd[level],&lmean[level]) == EOF){
        show_err_msg("Error reading pgstudy.dat - ABORTING - press any key.");
        quit( );
        }
        }
        fclose(fp);
}
/* this routine will write the peer group study data to a file named
pgstudy.dat.
The parameters gmean[ ],gsd[ ]and lmean[ ] must all be double arrays
of length 3 which are loaded respectively with group mean data,
group SD data, and lab mean data for each level.
void    write_study_stats(double gmean[ ],double gsd[ ],double lmean[ ]){
        FILE *fp;       /*File Pointer for Data File */
        int level;      /*Level of Control */
        printf("Writing pgstudy.dat\n");
        fp = fopen("pgstudy.dat","w");
        if(fp ==NULL){
        show_err_msg(
        "Cannot open pgstudy.dat - ABORTING - press any key."
        );
        quit( );
        }
        for(level=0;level<3;level++){
        if(fprintf(fp,"%lf\n%lf\n%1f\n",gmean[level],gsd[level],
           lmean[level]) == EOF){
           show_err_msg(
              "Error writing pgstudy.dat - ABORTING - press any key."
           );
           quit( );
           }
        }
        fclose(fp);
}
/* this routine will calculate the laboratory SDI from the group means,
group SD's, and lab means. It uses the formula SDI = (lmean - gmean)/gSD
The parameters gmean[ ],gsd[ ],lmean[ ] and lsdi must all be double arrays
of length 3, loaded respectively with group mean data,
group SD data, lab mean data for each level. lsdi will be loaded with the
generated laboratory standard deviation indexs    */
void calc_sdis(double gmean[ ],double gsd[ ],double lmean[ ],double lsdi[ ]){
        int level;      /* Level of Control */
        for(level = 0;level <3; level ++){
        if(gsd[level] != 0.0)
        lsdi[level] = (lmean[level] - gmean[level])/gsd[level];
        else
        lsdi[level] = 0.0;
        }
}
/* this routine will draw a dot 5 pixels wide at the current position.
If the file MONO.FLG exists in the current directory, the 2 pixel
border will be white and the interior will be black, otherwise the
border will be black and the interior white.    */
void draw_dot(void){
        if(access("MONO.FLG",0) != 0){
        setcolor(BLACK);
        circle(getx( ),gety( ),5);
        setfillstyle(SOLID_FILL,BLACK);
        floodfill(getx( ),gety( ),BLACK);
        setcolor(WHITE);
        circle(getx( ),gety( ),3);
        setfillstyle(SOLID_FILL,WHITE);
        floodfill(getx( ),gety( ),WHITE);
        setcolor(BLACK);
        }
        else{
        setcolor(WHITE);
```

```
        circle(getx( ),gety( ),5);
        setfillstyle(SOLID_FILL,WHITE);
        floodfill(getx( ),gety( ),WHITE);
        setcolor(BLACK);
        circle(getx( ),gety( ),3);
        setfillstyle(SOLID_FILL,BLACK);
        floodfill(getx( ),gety( ),BLACK);
        setcolor(WHITE);
    }
}
/* this routine will plot the lab SDI's on the Yundt plot.
The lsdi array should contain the SDI (as a double) for each level of
control.
If the file MONO.FLG exists in the current directory, the line will be
drawn in white, otherwise black will be used. */
void plot_yp(double lsdi[ ]){
    int max_x; /* Number of horizontal pixels */
    int max_y; /* Number of vertical pixels */
    int disp_l1; /* Level 1 pixel displacement */
    int disp_l2; /* Level 2 pixel displacement */
    int disp_l3; /* Level 3 pixel displacement */
    max_x = getmaxx( );
    max_y = getmaxy( );
    /* use a thick line */
    setlinestyle(SOLID_LINE,0,THICK_WIDTH);
    if(access("MONO.FLG",0) != 0)
    setcolor(BLACK);
    else
    setcolor(WHITE);
    /* draw displacement line */
    disp_l1 = (int)(lsdi[0]*(double)(max_x/10));
    moveto(4*max_x/10 + disp_l1,max_y/8);
    disp_l2 = (int)(lsdi[1]*(double)(max_x/10));
    lineto(4*max_x/10 + disp_l2,4*max_y/8);
    disp_l3 = (int)(lsdi[2]*(double)(max_x/10));
    lineto(4*max_x/10 + disp_l3,7*max_y/8);
    /* plot SDI points */
    draw_dot( );
    moveto(4*max_x/10 + disp_l2,4*max_y/8);
    draw_dot( );
    moveto(4*max_x/10 + disp_l1,max_y/8);
    draw_dot( );
}
/* this routine will exit graphics mode and leave the program */
int quit(void){
restorecrtmode( );
exit(0);
return 0;     /* to alleviate compiler warnings. */
}
/* this routine will ask the user if they want to enter new data and
returns TRUE if the user hits 'y' or 'Y'. Otherwise FALSE is returned. */
int do_more(void){
    int ret; /* TRUE for Y, FALSE otherwise */
    setcolor(WHITE);
    outtextxy(0,8,"Press Y to enter new data - anything else to exit.");
    if(toupper(getch( )) == 'Y'
    ret = TRUE;
    else
    ret = FALSE;
    outtextxy(0,8,"
    return ret;
}
/* this routine will get a new mean from the user. The user inputs data
until a -1 is encountered. The mean parameter is assigned the average
of the entered data.     */
void get_lab_mean(double *mean){
    int count; /* Number of datapoints read */
    double data; /* Last datapoint read    */
    double sum; /* Sum of datapoints read */
    printf("Enter new datapoints. Use -1 to end input.\n");
    sum = 0.0;
    count = 1;
    printf("       Enter datapoint %2d:",count);
    scanf("%lf",&data);
    while(data != -1.0){
    sum += data;
    *mean = sum/(double)count;
    printf("Mean = %8.2lf. Enter datapoint %2d:",*mean,++count);
    scanf("%lf",&data);
    }
```

```
}
/* this routine will display the current group and laboratory means for
each level and ask the user if they wish to alter them. A response
of 'Y' and 'y' will call get_lab_mean( ) for a new mean.    */
void get_new_lmeans(double gmean[ ], double lmeans[ ]){
    printf(
    "The current lab mean for level I is %8.2lf. Group mean = %8.2lf.\n"
    ,lmean[0],gmean[0]
    );
    printf("Do you wish to enter new level I data (Y/N) ?\n");
    if(toupper(getch( )) == 'Y'){
    get_lab_mean(&lmean[1]);
    }
    printf(
    "The current lab mean for level II is %8.2lf.Group mean = %8.2lf.\n"
    ,lmean[1],gmean[1]
    );
    printf("Do you wish to enter new level II data (Y/N) ?\n");
    if(toupper(getch( )) = 'Y'){
    get_lab_mean(&lmean[1]);
    }
    printf(
    "The current lab mean for level III is %8.2lf.Group mean = %8.2lf.\n"
    ,lmean[2],gmean[2]
    );
    printf("Do you wish to enter new level III data (Y/N) ?\n");
    if(toupper(getch( )) = 'Y'){
    get_lab_mean(&lmean[2]);
    }
}
/* this routine displays a help screen. */
void print_help_screen(void){
    printf("This program uses a Yundt Plot to assess instrument calibration.\n");
    printf("A peer-group study using 3 levels of control materials should be\n");
    printf("conducted to generate a laboratory mean as well as group means\n");
    printf("and group SD's for each level of control used.\n\n");
    printf("This data should be placed in a file named \"pgstudy.dat\" ");
    printf("in the format:\n");
    printf("  level_1_group_mean level_1_group_sd level_1_lab_mean\n");
    printf("  level_2_group_mean level_2_group_sd level_2_lab_mean\n");
    printf("  level_3_group_mean level_3_group_sd level_3_lab_mean\n\n");
    printf("The program will display the information as a Yundt Plot.\n\n");
    printf("If the Yundt Plot points fall to the right of the center line,\n");
    printf("the instrument should be adjusted lower.\n\n");
    printf("If the Yundt Plot points fall to the left of the center line,\n");
    printf("the instrument should be adjusted higher.\n\n");
    printf("The goal is to achieve a straight line down the center.\n");
    printf("The colored regions denote the severity of a displacement.\n\n");
    printf("After adjusting the instrument, evaluate more control specimens\n");
    printf("and enter them into the system to see the significance of the\n");
    printf("adjustment.\n");
    printf("Press any key to continue. . .");
    getch( );
}
int main(void){
    double gmean[3]; /* Group Mean for 3 Control Levels */
    double gsd[3];   /* Group SD for 3 Control Levels */
    double lmean[3]; /* Lab Mean for 3 Control Levels */
    double lsdi[3];  /* Lab SDI for 3 Control Levels */
    print_help_screen( );
    read_study_stats(gmean,gsd,lmean);
    init_graphics( );
    draw_yp_outline( );
    calc_sdis(gmean,gsd,lmean,lsdi);
    plot_(lsdi);
    while(do_more( )){
        restorecrtmode( );
        get_new_lmeans(gmean,lmean);
        write_study_stats(gmean,gsd,lmean);
        init_graphics( );
        calc_sdis(gmean,gsd,lmean,lsdi);
        draw_yp_outline( );
        plot_yp(lsdi);
    }
    return quit( );
}
```

The program is written for BORLAND C++, Version 3.1. The program reads from a data file containing the data points to be plotted. It also will be appreciated by those skilled in the art that the above computer program is to be employed to configure a general purpose microprocessor to create specific logic circuits. Thus, the present invention encompasses a programmed computer system for analyzing the performance of a testing device for analyzing biochemical samples which operates over multiple ranges. Further, this computer-executable program code is to be stored on a computer-readable memory so that the memory is capable of implementing the method of plotting and analyzing data for multilevel control system testing devices according to the present invention. In this regard, the computer-readable memory of the present invention includes a data structure for forming generally parallel spaced apart data ranges axes, each relating to a range of operation of the testing device, to facilitate analysis of the performance of the testing device over each range of operation. The computer memory also includes structure for plotting deviation indexes for the testing device in relation to the data range axes in such a way that analysis of the performance of the testing device is provided in a single graphic display.

After a graph, such as one of the graphs shown in FIGS. 4-9, is generated, the performance of the multilevel control system device can be analyzed over all operational ranges. The device being analyzed can thereafter be calibrated to correct any performance error that might be shown on the graph. Such calibration techniques vary depending on the particular device being analyzed. Nevertheless, such calibration techniques are well known in the art.

Figure 10:
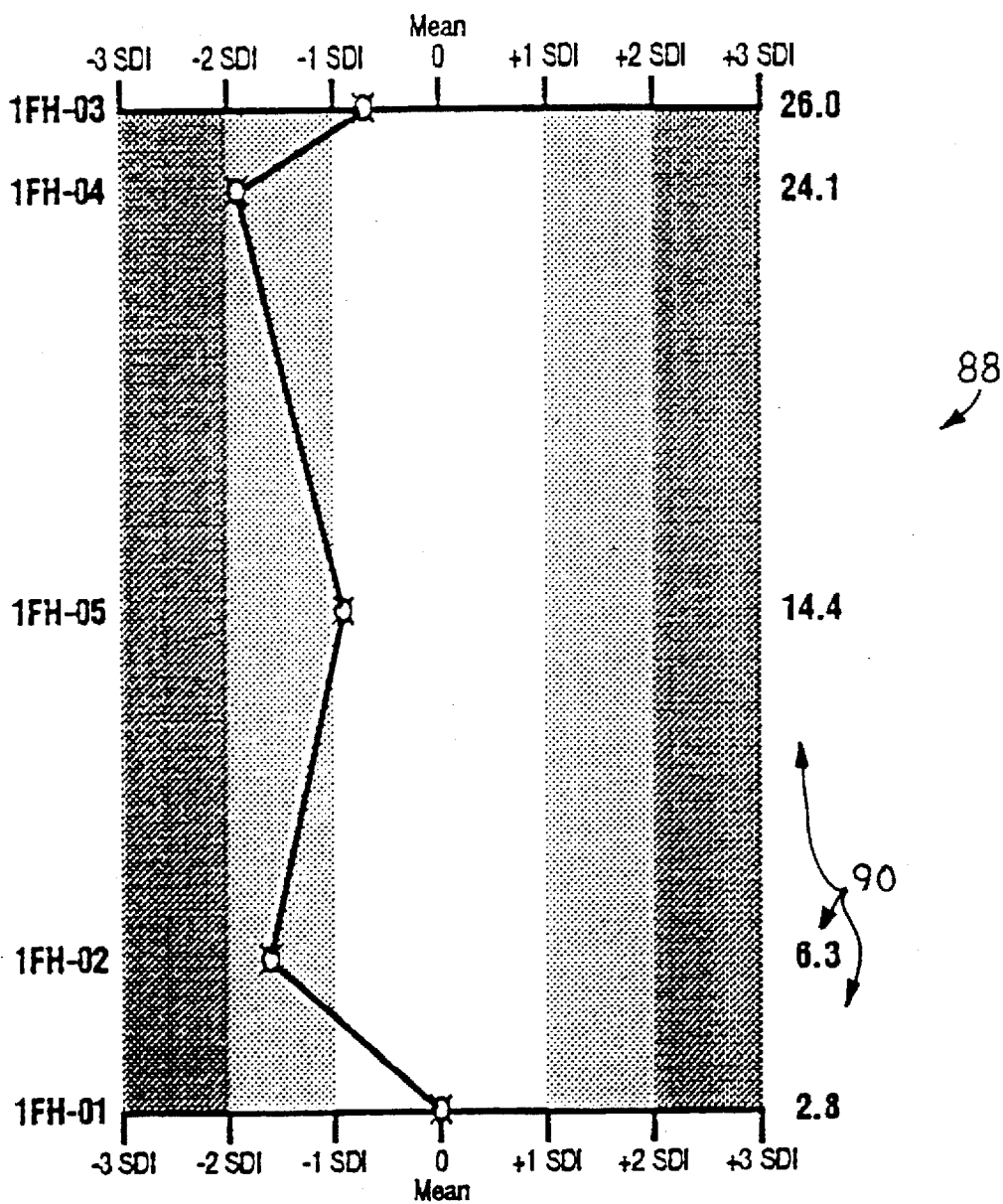
FIG. 10 shows another preferred embodiment of the graph of the present invention used in the method for analyzing the performance of a multilevel control system device.
Figure 11:
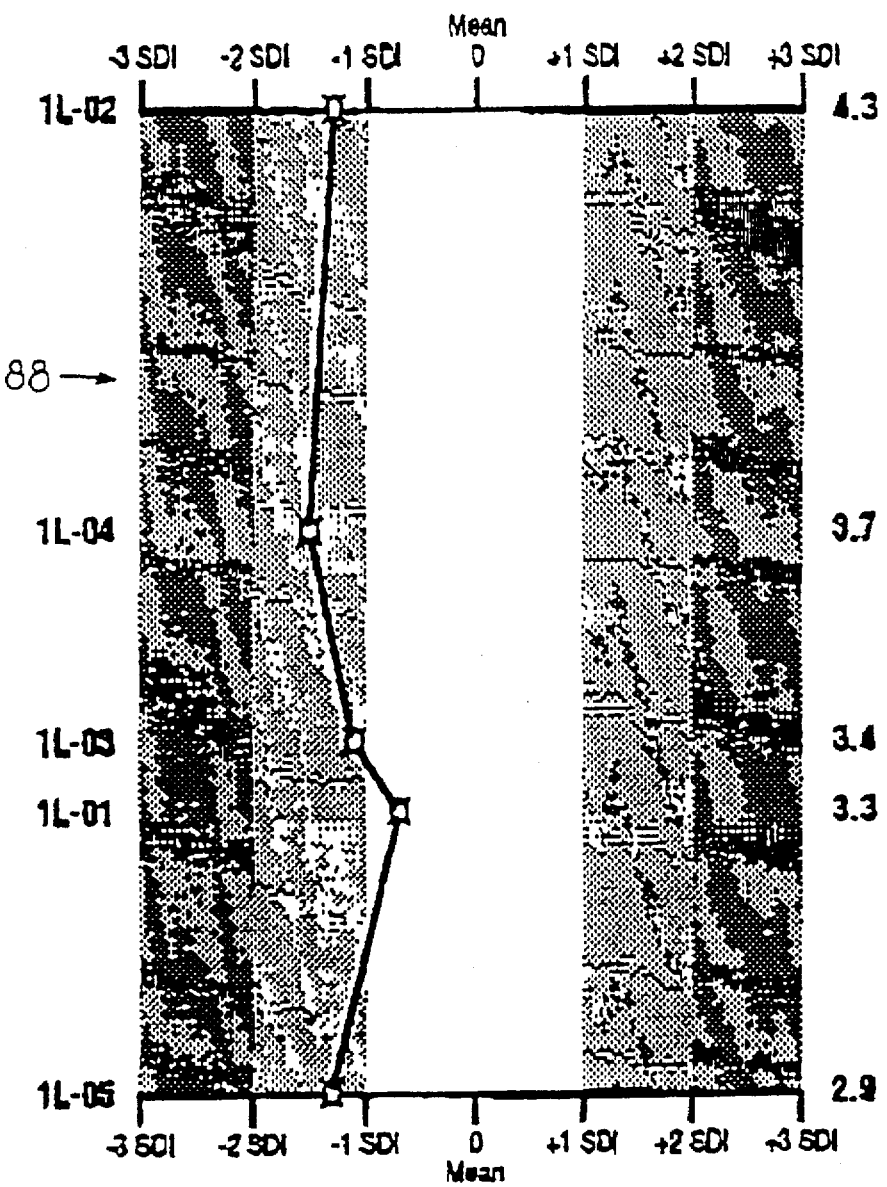
FIG. 11 shows the method step of plotting data from a multilevel control system device on the graph of FIG. 10.
Figure 12:
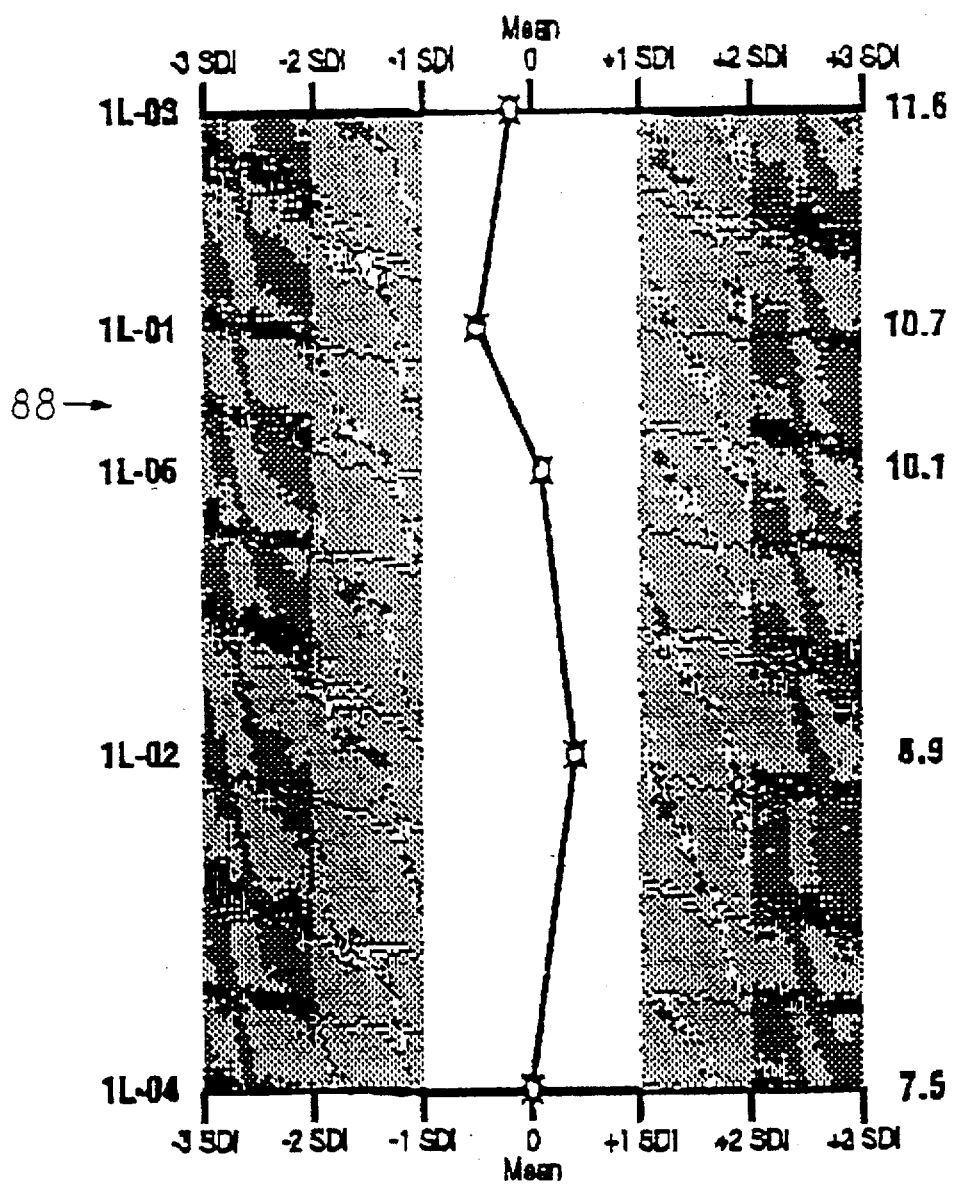
FIG. 12 shows the method step of plotting data from a multilevel control system device on the graph of FIG. 10.

Referring now to FIGS. 10, 11 and 12, a second preferred embodiment of the method for analyzing the performance of a testing device is shown. The graph 88 shown in FIGS. 10, 11 and 12 is similar to that shown in FIGS. 4-8. However, in graph 88, the respective positions of the data range axes are scaled in relation to one another based on the values of the operating ranges. This enables a user to more accurately determine the significance of the differences between specimen SDI values. For example, in FIG. 10, five specimen means are plotted on graph 88. The values for the specimen means are designated generally by reference numeral 90. As can be seen, the specimen 1FH-01 has a value of 2.8, the specimen 1FH-02 has a value of 6.3, and the specimen 1FH-05 has a value of 14.4. As is apparent, the data range axes for the these specimen are scaled in relation to one another such that the spacing between the data range axes representing specimen 1FH-01 and 1FH-02 is closer than the corresponding spacing between specimen 1FH-02 and 1FH-05.

As noted, this scaled positioning of the data range axes provides a greater level of understanding relative to the differences between SDI values for specimens or at various operating ranges. For example, still referring to FIG. 10, the difference in the SDI values between points 1FH-03 and 1FH-04 indicates that there is a precision problem relating to the testing device since the values of the operating ranges are close to one another. By contrast, the difference in the SDI value between points 1FH-04 and 1FH-05 indicates a linearity problem because the testing device behaves differently at different operational ranges or at different concentration levels of specimens.

The graphs of FIGS. 11 and 12 are similar to that shown in FIG. 10 but indicate differences in the scaled relation of the vertical positions of the multiple data range axes based on the values of the operating ranges. In order to scale the vertical spacing between the data range axes representing the various operating ranges of the testing device, the following method should be utilized:

Let the horizontal width of the plot be represented by HW.
Let the vertical height of the plot be represented by VH.
Sort the data pairs in ascending order according to the specimen mean value of the data pair to determine the specimen with the lowest mean and the specimen with the highest mean.
Let the mean value of the lowest specimen mean be represented by LO.
Let the mean value of the highest specimen mean be represented by HI.
The x coordinate for any data pair is determined by the specimen SDI value. It is given by x=specimen_SDI_value*HW/6+HW/2.
The y coordinate for any data pair is determined by the specimen mean value. It is given by y=(specimen_mean_value–LO)*VH/(HI–LO).

Figure 13:
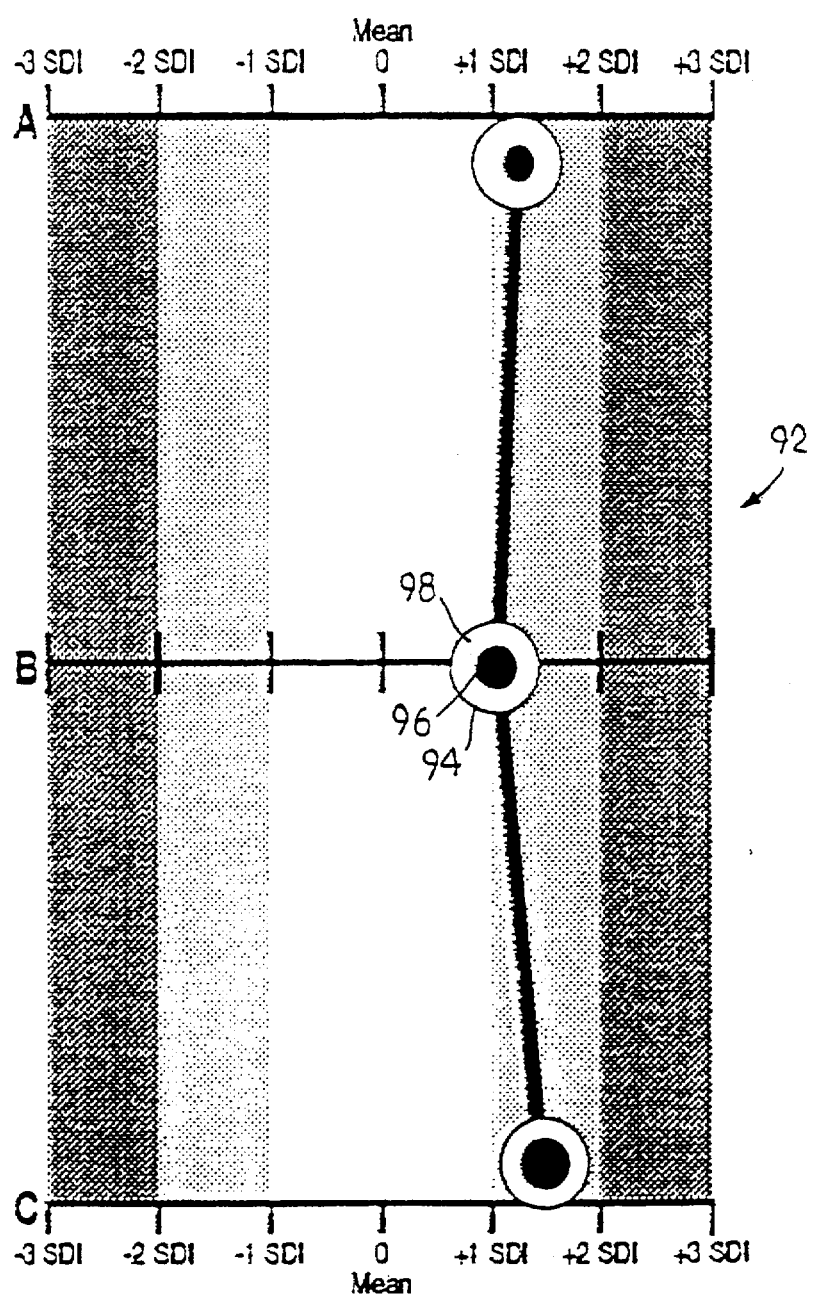
FIG. 13 shows yet another preferred embodiment of the graph of the present invention used in the method for analyzing the performance of a multilevel control system device.
Figure 14:
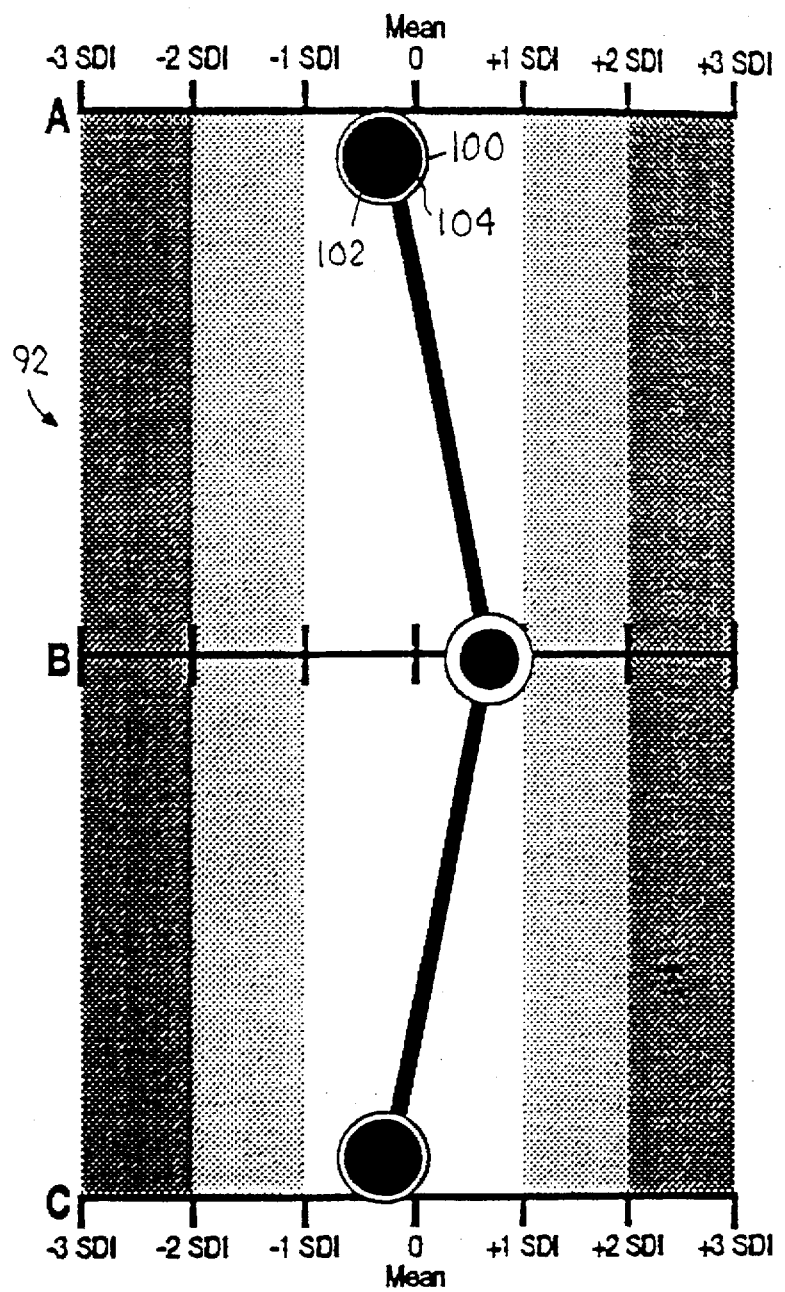
FIG. 14 shows the method step of plotting data from a multilevel control system device on the graph of FIG. 13.
Figure 15:
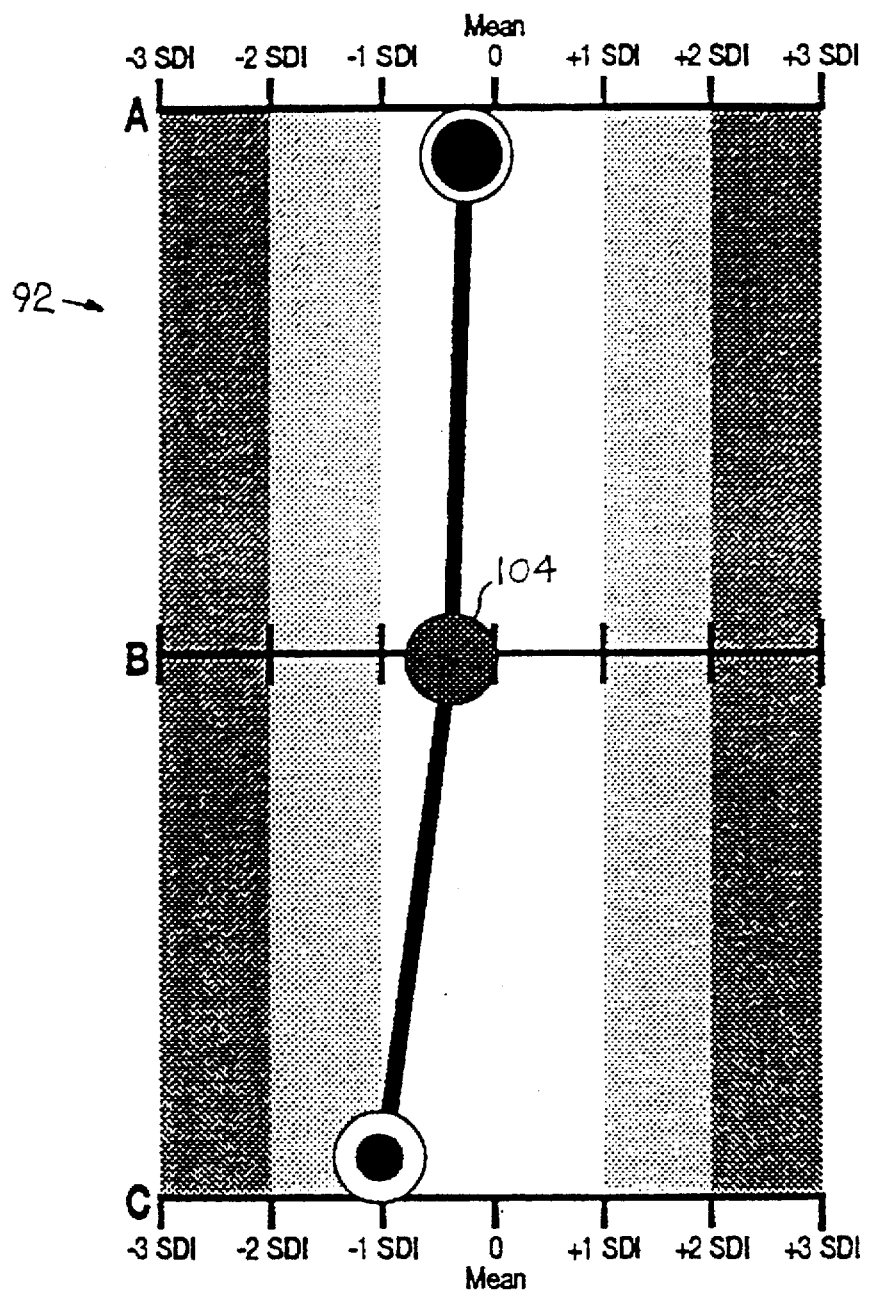
FIG. 15 shows the method step of plotting data from a multilevel control system device on the graph of FIG. 13.

FIGS. 13–15 represent still another preferred embodiment of the method for analyzing the performance of testing devices according to the present invention. Referring to FIG. 13, a graph 92 is depicted which is similar to the graphs shown in FIGS. 4–8. However, the graph 92 includes additional information relating to the Coefficient of Variation (CV) for the group of testing devices and the individual testing device. More specifically, graph 92 includes a plot point 94 on one of the data range axes of the graph. Plot point 94 is a plot point of the individual CV imposed on a plot point of the group CV.

As shown in FIG. 13, plot point 94 includes a black region 96 which represents the individual CV value and a white region 98 which represents the group CV value. The relative sizes of the white and black regions 96 and 98 indicate how close the individual CV is to the group CV. In plot point 94, the fact that region 96 is surrounded by region 98 indicates that the individual CV is smaller than the group CV. In FIG. 14, for example, plot point 100 includes a black region 102 that nearly encompasses the entire plot point such that there is only a small white region 104. Thus, plot point 100 indicates that the CV value of the individual testing device is closer to the group CV value than is the case with plot point 94.

In FIG. 15, a plot point 104 is shown having gray shading. The gray shading of plot point 104 indicates that the individual CV and the group CV are within five percent of each other. Additionally, although not shown in FIGS. 13–15, the positions of the data range axes A, B and C can be scaled in relation to one another similar to the graphs shown in FIGS. 10–12.

Thus, it can be seen that the graphs of the present invention and the methods of plotting and analyzing data for multilevel control system devices thereon facilitate analysis of the performance of one device or multiple devices over all ranges of operation. It should be understood that a data range axis is formed on the graph for each range of performance for a particular device, and thus a plurality of data range axes corresponding to each range of performance of a device can be provided so that analysis of the performance of a device can be performed for every range of performance of the device. Additionally, in accordance with the present invention, the respective positions of the data range axes can be scaled in relation to one another based on the values of the operating ranges to provide addtional information concerning the performance of the testing device. Further, the plot of the deviation indexes can include a visual indication of the Coefficient of Variation (CV) of the group of testing devices in comparison to the CV of the individual testing device.

From the foregoing, it will be seen that this invention is one well-adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

I claim:

1. A method for analyzing the performance of a testing device for analyzing human bodily fluids which operates over at least two ranges, the method comprising:

obtaining a first set of test results relating to human bodily fluids from the testing device over at least two ranges;

calculating from the first set of test results an individual range mean for each of the at least two ranges;

obtaining a second set of test results relating to human bodily fluids from a group of testing devices that operate over the at least two ranges;

calculating from the second set of test results a group range mean and a group range standard deviation for each of the at least two ranges;

calculating standard deviation indexes for the testing device from the individual range means, the group range means and the group range standard deviations;

forming generally parallel spaced apart data range axes, each relating to a range of operation of the testing device, to facilitate analysis of the performance of the testing device over each range of operation, wherein the respective positions of the data range axes in relation to one another are scaled based on the values of the operating ranges; and plotting all of the standard deviation indexes in relation to the data range axes in such a way that analysis of the performance of the testing device over the at least two operating ranges is provided in a single graphic display.

2. The method of claim 1 further comprising labeling at least one of the data range axes with standard deviation index (SDI) units.

3. The method of claim 2 further comprising labeling a zero reference point along at least one of the data range axes, and labeling in one direction along at least one of the data range axes with positive increments of the SDI units, and labeling in the other direction along at least one of the data range axes with negative increments of the SDI units.

4. The method of claim 3 further comprising labeling the zero reference point with 0, labeling the positive increments with +1 and +2 SDI units, and labeling the negative increments with −1 and −2 SDI units so that regions are created between adjacent SDI units.

5. The method of claim 4 further comprising forming a first visible indicia within the regions between 0 and +1 or −1 SDI units, forming a second visible indicia within the regions between +1 or −1 SDI units and +2 or −2 SDI units, respectively, and forming a third visible indicia within the regions beyond the +2 or −2 SDI units, to uniquely identify the regions.

6. The method of claim 5 wherein the first, second, and third visible indicia comprise different shadings.

7. The method of claim 1 wherein the step of plotting the standard deviation indexes includes providing a visual indication of the Coefficient of Variation (CV) of the group of testing devices in comparison to the CV of the individual testing device.

8. The method of claim 7 wherein the visual indication comprises a plot point at each of the data range axes, the plot point including a plot point of the individual CV imposed on a plot point of the group CV.

9. The method of claim 8 wherein the plot point is circular, and wherein the plot point of the group CV comprises a white region, and the plot point of the individual CV comprises a shaded region, wherein the relative sizes of the respective group CV and individual CV plot points imposed on one another provide a comparison of the values between said group CV and individual CV.

10. The method of claim 1 wherein the step of plotting comprises plotting the data using a computer program.

11. The method of claim 10 further comprising analyzing the plotted data, and calibrating the testing device based upon the analysis.

12. The method of claim 1 wherein the testing device comprises a hematology testing device.

13. The method of claim 1 further comprising forming an axis in generally orthogonal relation to the data range axes.

14. The method of claim 1 further comprising analyzing the plotted data, and calibrating the testing device based upon the analysis.

15. A method for analyzing the performance of a testing device for analyzing biochemical samples which operates over at least two ranges, the method comprising:

obtaining a first set of test results relating to a biochemical sample from the testing device over at least two ranges;

obtaining a second set of test results relating to the biochemical sample from a group of testing devices that operate over the at least two ranges;

calculating deviation indexes for the testing device from the first set of test results and the second set of test results by determining the deviation of the performance of the testing device from that of the group of testing devices for each of the at least two ranges and unitizing the deviations;

forming generally parallel spaced apart data range axes, each relating to a range of operation of the testing device, to facilitate analysis of the performance of the testing device over each range of operation, the respective positions of the data range axes being scaled in relation to one another based on the values of the operating ranges; and plotting all of the deviation indexes in relation to the data range axes in such a way that analysis of the performance of the testing device over the at least two operating ranges is provided in a single graphic display.

16. The method of claim 15 further comprising labeling a zero reference point along at least one of the data range axes, and labeling in one direction along the data range axes with positive increments of the deviation index units, and labeling in the other direction along at least one of the data range axes with negative increments of the deviation index units.

17. The method of claim 15 wherein the testing device comprises a device for analyzing human bodily fluids.

18. The method of claim 15 wherein the testing device comprises a hematology testing device.

19. The method of claim 15 wherein the step of plotting the deviation indexes includes providing a visual indication of the Coefficient of Variation (CV) of the group of testing devices in comparison to the CV of the individual testing device.

20. The method of claim 19 wherein the visual indication comprises a plot point at each of the data range axes, the plot point including a plot point of the individual CV imposed on a plot point of the group CV.

21. The method of claim 20 wherein the plot point is circular, and wherein the plot point of the group CV comprises a white region, and the plot point of the individual CV comprises a shaded region, wherein the relative sizes of the respective group CV and individual CV plot points imposed on one another provide a comparison of the values between said group CV and individual CV.

22. A graph for analyzing the performance of a testing device for analyzing biochemical samples which operates over a least two ranges, wherein the graph is formed using a computer program, the graph comprising:

at least two generally parallel spaced apart data range axes each relating to a range of operation of the testing device for facilitating analysis of the performance of the testing device over each range of operation, the respective positions of the data range axes being scaled in relation to one another based on the values of the operating ranges; and a plot of deviation indexes formed by the computer program for the testing device along the data range axes, wherein the graph provides analysis of the performance of the testing device over each range of operation in a single graphic display.

23. The graph of claim 22 wherein said deviation indexes comprise standard deviation indexes, and further comprising standard deviation index (SDI) unit indicia for at least one of the data range axes.

24. The graph of claim 23 wherein the data range axes comprise a midpoint and the SDI unit indicia comprise zero SDI unit indicia corresponding to the midpoint, positive increments of the SDI units beyond the midpoint on one side of the data range axes, and negative increments of the SDI units beyond the midpoint on the other side of the data range axes.

25. The graph of claim 24 wherein the positive increments comprise +1 and +2 SDI unit indicia and the negative increments comprise −1 and −2 SDI unit indicia, such that regions are formed between adjacent SDI unit indicia.

26. The graph of claim 25 further comprising a first visible indicia within the regions between 0 and +1 or −1 SDI units, a second visible indicia within the regions between +1 or −1 SDI units and +2 or −2 SDI units, respectively, and a third visible indicia within the regions beyond the +2 or −2 SDI units, to uniquely identify the regions.

27. The graph of claim 26 wherein the first, second, and third indicia comprise different shadings.

28. The graph of claim 22 wherein said testing device comprises a hematology testing device.

29. The graph of claim 22 wherein said graph further comprises an axis in generally orthogonal relation to the data range axes.

30. The graph of claim 22 wherein the plot of the deviation indexes includes a visual indication of the Coefficient of Variation (CV) of a group of testing devices in comparison to the CV of the individual testing device.

31. The graph of claim 30 wherein the visual indication comprises a plot point at each of the data range axes, the plot point including a plot point of the individual CV imposed on a plot point of the group CV.

32. The graph of claim 31 wherein the plot point is circular, and wherein the plot point of the group CV comprises a white region, and the plot point of the individual CV comprises a shaded region, wherein the relative sizes of the respective group CV and individual CV plot points imposed on one another provide a comparison of the values between said group CV and individual CV.

33. A method for analyzing the performance of a testing device for analyzing biochemical samples which operates over at least two ranges, the method comprising:

obtaining a first set of test results relating to a biochemical sample from the testing device over at least two ranges;

obtaining a second set of test results relating to the biochemical sample from a group of testing devices that operate over the at least two ranges;

calculating deviation indexes for the testing device from the first set of test results and the second set of test results by determining the deviation of the performance of the testing device from that of the group of testing devices for each of the at least two ranges and unitizing the deviations;

forming generally parallel spaced apart data range axes, each relating to a range of operation of the testing device, to facilitate analysis of the performance of the testing device over each range of operation; and plotting all of the deviation indexes in relation to the data range axes in such a way that analysis of the performance of the testing device over the at least two operating ranges is provided in a single graphic display, wherein the plotting includes a visual indication of the Coefficient of Variation (CV) of the group of testing devices in comparison to the CV of the testing device.

34. The method of claim 33 wherein the visual indication comprises a plot point at each of the data range axes, the plot point including a plot point of the individual CV imposed on a plot point of the group CV.

35. The method of claim 34 wherein the plot point is circular, and wherein the plot point of the group CV comprises a white region, and the plot point of the individual CV comprises a shaded region, wherein the relative sizes of the respective group CV and individual CV plot points imposed on one another provide a comparison of the values between said group CV and individual CV.

36. A computer-readable memory having stored therein computer-executable program code for implemeting with a computer a method for analyzing the performance of a testing device for analyzing biochemical samples which operates over at least two ranges, the computer-readable memory comprising:

structure for forming at least two generally parallel spaced apart data range axes each relating to a range of operation of the testing device for facilitating analysis of the performance of the testing device over each range of operation, and structure for plotting deviation indexes formed by the computer program for the testing device in relation to the data range axes in such a way that analysis of the performance of the testing device over each range of operation is provided in a single graphic display.

37. The computer-readable memory of claim 36 wherein the respective positions of the data range axes are scaled in relation to one another based on the values of the operating ranges.

38. The computer-readable memory of claim 36 wherein the plot of deviation indexes includes a visual indication of the Coefficient of Variation (CV) of the group of testing devices in comparison to the CV of the testing device.

39. The computer-readable memory of claim 38 wherein the visual indication comprises a plot point at each of the data range axes, the plot point including a plot point of the individual CV imposed on a plot point of the group CV.

40. The computer-readable memory of claim 39 wherein the plot point is circular, and wherein the plot point of the group CV comprises a white region, and the plot point of the individual CV comprises a shaded region, wherein the relative sizes of the respective group CV and individual CV plot points imposed on one another provide a comparison of the values between said group CV and individual CV.

* * * * *

UNITED STATES PATENT AND TRADEMARK OFFICE
CERTIFICATE OF CORRECTION

PATENT NO. : 5,734,591
DATED      : March 31, 1998
INVENTOR(S): John C. Yundt

It is certified that error appears in the above-indentified patent and that said Letters Patent is hereby corrected as shown below:

At column 20, line 39, the word "sealed" should read --scaled--.

Signed and Sealed this

Second Day of June, 1998

BRUCE LEHMAN

Attest:

Attesting Officer

Commissioner of Patents and Trademarks